(12) United States Patent
Zarra et al.

(10) Patent No.: US 12,048,520 B2
(45) Date of Patent: Jul. 30, 2024

(54) ELECTRODE APPARATUSES AND METHODS OF FORMING ELECTRODE APPARATUSES

(71) Applicant: Nokia Technologies Oy, Espoo (FI)

(72) Inventors: Salvatore Zarra, Bordentown, NJ (US); Mingde Zheng, Bridgewater, NJ (US)

(73) Assignee: Nokia Technologies Oy, Espoo (FI)

( * ) Notice: Subject to any disclaimer, the term of this patent is extended or adjusted under 35 U.S.C. 154(b) by 271 days.

(21) Appl. No.: 16/889,456

(22) Filed: Jun. 1, 2020

(65) Prior Publication Data

US 2020/0397337 A1 Dec. 24, 2020

(30) Foreign Application Priority Data

Jun. 20, 2019 (EP) ..................................... 19181535

(51) Int. Cl.
*A61B 5/0531* (2021.01)
*A61B 5/25* (2021.01)
*B01L 3/00* (2006.01)

(52) U.S. Cl.
CPC .............. *A61B 5/0531* (2013.01); *A61B 5/25* (2021.01); *B01L 3/502707* (2013.01); *B01L 3/50273* (2013.01)

(58) Field of Classification Search
CPC ......... A61B 5/0531; A61B 5/25; A61B 5/318; A61B 5/368; A61B 5/389; A61L 3/502707; A61L 3/50273
See application file for complete search history.

(56) References Cited

U.S. PATENT DOCUMENTS

| 8,197,775 | B2 | 6/2012 | Johnston et al. |
| 9,167,684 | B2 | 10/2015 | Allen et al. |
| 2004/0059405 | A1 | 3/2004 | White et al. |
| 2004/0096959 | A1* | 5/2004 | Stiene ............... A61B 5/150419 435/287.2 |
| 2006/0000709 | A1* | 1/2006 | Bohm ............... B01L 3/502738 422/68.1 |
| 2013/0243655 | A1 | 9/2013 | Li et al. |

(Continued)

FOREIGN PATENT DOCUMENTS

| EP | 1362827 A1 | 11/2003 |
| WO | WO-2019/060689 A1 | 3/2019 |
| WO | WO-2019/090161 A1 | 5/2019 |

OTHER PUBLICATIONS

"3M Red Dot ECG Electrodes Foam Tape Sticky Gel 2560", USA Medical and Surgical Supplies, Retrieved on May 29, 2020, Webpage available at : https://www.usamedicalsurgical.com/3m-red-dot-ecg-electrodes-foam-tape-sticky-gel-2560/.

(Continued)

*Primary Examiner* — Rebecca C Bryant
(74) *Attorney, Agent, or Firm* — Harrington & Smith (57) ABSTRACT

An electrode apparatus comprising: a substrate, the substrate comprising: a first microfluidic channel; a second microfluidic channel; and at least one conduit extending between the first microfluidic channel and the second microfluidic channel; wherein the first microfluidic channel and the at least one conduit comprise electrically conductive material, and wherein the second microfluidic channel is exposed to the external environment and configured to absorb liquid by capillary action.

20 Claims, 6 Drawing Sheets

(56) References Cited

U.S. PATENT DOCUMENTS

| | | |
|---|---|---|
| 2016/0256070 A1 | 9/2016 | Murphy et al. |
| 2016/0361015 A1 | 12/2016 | Wang et al. |
| 2017/0056682 A1 | 3/2017 | Kumar et al. |
| 2019/0032021 A1 | 1/2019 | Ingber et al. |
| 2021/0000395 A1* | 1/2021 | Rogers ............... A61B 5/14539 |

OTHER PUBLICATIONS

Wang et al., "Novel Semi-Dry Electrodes for Brain-Computer Interface Applications", Journal of Neural Engineering, vol. 13, No. 4, Jul. 5, 2016, pp. 1-15.

"Water Electrode Inserts for Mobita EEG", Biopac, Retrieved on May 29, 2020, Webpage available at : https://www.biopac.com/product/water-electrode-inserts/.

Rawat et al., "Transdermal Delivery by Iontophoresis", Indian Journal of Pharmaceutical Sciences, vol. 70, No. 1, Jan.-Feb. 2008, 7 pages.

Reeder et al., "Waterproof, electronics-enabled, epidermal microfluidic devices for sweat collection, biomarker analysis, and thermography in aquatic settings", Science Advances, vol. 5, Jan. 25, 2019, pp. 1-13.

Kang et al., "Fabrication of truly 3D microfluidic channel using 3D-printed soluble mold", Biomicrofluidics, vol. 12, 2018, pp. 014105-1-014105-10.

Twine et al., "Open Nanofluidic Films with Rapid Transport and No Analyte Exchange for Ultra-low Sample Volumes", Lab on a Chip, vol. 18, Jul. 13, 2018, 10 pages.

Extended European Search Report received for corresponding European Patent Application No. 19181535.6, dated Dec. 10, 2019, 7 pages.

\* cited by examiner

ELECTRODE APPARATUSES AND METHODS OF FORMING ELECTRODE APPARATUSES

TECHNOLOGICAL FIELD

Embodiments of the present disclosure relate to electrode apparatuses and methods of forming electrode apparatuses. Some relate to electrode apparatuses and methods of forming electrode apparatuses configured to be used in biopotential measurements.

BACKGROUND

Biopotential measurements in the form of, for example, electrocardiograms (ECG) electroencephalograms (EEG), electrooculograms (EOG) and electromyograms (EMG) are used to monitor the activity of organs, for example the heart, brain, eyes and muscles.

Biopotential measurements can be made by placing non-invasive surface electrodes on the body.

In examples, it is beneficial for the electrodes to adhere well to the body part and to include electrolyte, such as an electrolyte layer, to enable better biopotential measurements to be obtained.

BRIEF SUMMARY

The scope of protection sought for various embodiments of the invention is set out by the independent claims. The examples and features, if any, described in this specification that do not fall under the scope of the independent claims are to be interpreted as examples useful for understanding various embodiments of the invention.

According to various, but not necessarily all, embodiments there is provided an electrode apparatus comprising:
a substrate, the substrate comprising:
  a first microfluidic channel;
  a second microfluidic channel; and
  at least one conduit extending between the first microfluidic channel and the second microfluidic channel;
  wherein the first microfluidic channel and the at least one conduit comprise electrically conductive material, and
  wherein the second microfluidic channel is exposed to the external environment and configured to absorb liquid by capillary action.

In some but not necessarily all examples the electrode apparatus comprises at least one first microfluidic channel and at least one second microfluidic channel.

In some but not necessarily all examples, the electrode apparatus comprises at least one reservoir configured to perform at least one of absorbing, by capillary action, liquid from the second microfluidic channel and supplying, by capillary action, liquid stored in the at least one reservoir to the second microfluidic channel.

In some but not necessarily all examples, the at least one reservoir comprises at least one microfluidic channel having a larger section than the second microfluidic channel.

In some but not necessarily all examples, the at least one reservoir comprises a plurality of connections to the second microfluidic channel.

In some but not necessarily all examples, the at least one reservoir is enclosed within the substrate. In some examples the at least one reservoir can be considered to be fully enclosed within the substrate.

In some but not necessarily all examples, the conduits narrow from the first microfluidic channel towards the second microfluidic channel.

In some but not necessarily all examples, the substrate is formed from at least one class of conformable and/or self-adhesive polymer material.

According to various, but not necessarily all, embodiments there is provided a method comprising:
forming a first microfluidic channel comprising electrically conductive material;
forming a second microfluidic channel; and
forming at least one conduit extending between the first microfluidic channel and the second microfluidic channel, the at least one conduit comprising electrically conductive material;
wherein the second microfluidic channel is exposed to the external environment and configured to absorb liquid by capillary action.

In some but not necessarily all examples, the method comprises forming at least one first microfluidic channel and forming at least one second microfluidic channel.

In some but not necessarily all examples, forming the first microfluidic channel and forming the at least one conduit comprises fabricating electrically conductive material in the form of the first microfluidic channel and at least one conduit.

In some but not necessarily all examples, forming the second microfluidic channel comprises fabricating removable mould material in the form of the second microfluidic channel.

In some but not necessarily all examples, the method comprises forming a substrate around the formed first microfluidic channel, second microfluidic channel and at least one conduit.

In some but not necessarily all examples, the method comprises removing the removable mould material.

In some but not necessarily all examples, forming the first microfluidic channel, the second microfluidic channel and the at least one conduit comprises:
  forming a substrate layer by layer to form the first microfluidic channel, the second microfluidic channel and at least one conduit; and
  providing electrically conductive material in the first microfluidic channel and the at least one conduit.

In some but not necessarily all examples, the method comprises forming at least one reservoir configured to perform at least one of absorbing, by capillary action, liquid from the second microfluidic channel and supplying, by capillary action, liquid stored in the at least one reservoir to the second microfluidic channel.

In some but not necessarily all examples, the at least one reservoir comprises at least one microfluidic channel having a larger section than the second microfluidic channel.

In some but not necessarily all examples, the at least one reservoir comprises a plurality of connections to the second microfluidic channel.

In some but not necessarily all examples, the at least one reservoir is enclosed within the substrate. In some examples the at least one reservoir can be considered to be fully enclosed within the substrate.

In some but not necessarily all examples, the conduits narrow from the first microfluidic channel towards the second microfluidic channel.

In some but not necessarily all examples, the substrate is formed from at least one class of conformable and/or self-adhesive polymer material.

According to various, but not necessarily all embodiments, there is provided a system comprising:
an apparatus for making one or more biopotential measurements; and at least one electrode apparatus as described herein.

In some but not necessarily all examples, the system comprises a plurality of electrode apparatuses as described herein.

According to various, but not necessarily all, embodiments there is provided a method comprising:
fabricating electrically conductive material in the form of a first microfluidic channel and at least one conduit;
fabricating removable mould material in the form of a second microfluidic channel;
forming a substrate around the formed first microfluidic channel, second microfluidic channel and at least one conduit; and
removing the removable mould material.

According to various, but not necessarily all, embodiments there is provided a method comprising:
forming a substrate layer by layer to form a first microfluidic channel and at least one conduit, the at least one conduit extending between the first microfluidic channel and a second microfluidic channel; and
introducing/providing electrically conductive material in the at least one first microfluidic channel and the at least one conduit.

BRIEF DESCRIPTION

Some examples will now be described with reference to the accompanying drawings in which.

DETAILED DESCRIPTION

Examples of the disclosure relate to an electrode apparatus 10 and method 600, 700 for forming an electrode apparatus 10.

In examples, the electrode apparatus 10 comprises a substrate 12, the substrate comprising a first microfluidic channel 14; a second microfluidic channel 16; and at least one conduit 18 extending between the first microfluidic channel 14 and the second microfluidic channel 16.

In examples, the first microfluidic channel 14 can be considered at least one first microfluidic channel 14.

In examples, the second microfluidic channel 16 can be considered at least one second microfluidic channel 16.

In examples, the first microfluidic channel 14 and the at least one conduit 18 comprise electrically conductive material 20, and the second microfluidic channel 16 is exposed to the external environment 22 and configured to absorb liquid 24 by capillary action.

In examples, the at least one conduit 18 comprising electrically conductive material 20 is configured to operate as an electrode or micro-electrode.

In examples, the second microfluidic channel 16 is configured to absorb and retain liquid 24, such as a liquid electrolyte, sweat, water, adjacent to the at least one conduit 18 to assist in, for example, biopotential measurements.

In examples, the second microfluidic channel 16 is exposed to the external environment 22 to allow the second microfluidic channel 16 to absorb, by capillary action, liquid from the external environment 22. In examples, the external environment can be considered to be the environment external to the electrode apparatus 10.

For example, the second microfluidic channel 16 can be configured to absorb, by capillary action, sweat from a subject when the electrode apparatus 10 is placed on the subject's body to make biopotential measurements.

The substrate 12 of the electrode apparatus 10 can be formed from material that can conform and adhere to a subject's body without any additives or adhesives.

The electrode apparatus 10 can therefore be configured to be reusable without the need for adhesive, which can dry out after multiple uses, which is advantageous.

The electrode apparatus 10 is also advantageous as the second microfluidic channel 16 is configured to continually provide and/or retain liquid adjacent the at least one conduit 18 to provide functionality equivalent to a micro-wet-electrode.

Furthermore, the electrode apparatus 10 provides for a high density of electrodes for use in, for example, biopotential measurements.

Examples of the disclosure therefore provide an electrode apparatus 10 which does not comprise a gel electrolyte layer that can dry out and also adheres well without the use of an adhesive layer which can result in discomfort for a subject.

In addition, examples of the disclosure provide a sustained, impedance controlled, long-term operating electrode skin interface that is easy to put on and take off.

This is beneficial in, for example, applications that require long-term continuous monitoring of biopotential measurements or other applications where an electrode is placed and removed many times. For example, in applications such as smart clothing and wearable devices.

Figure 1:
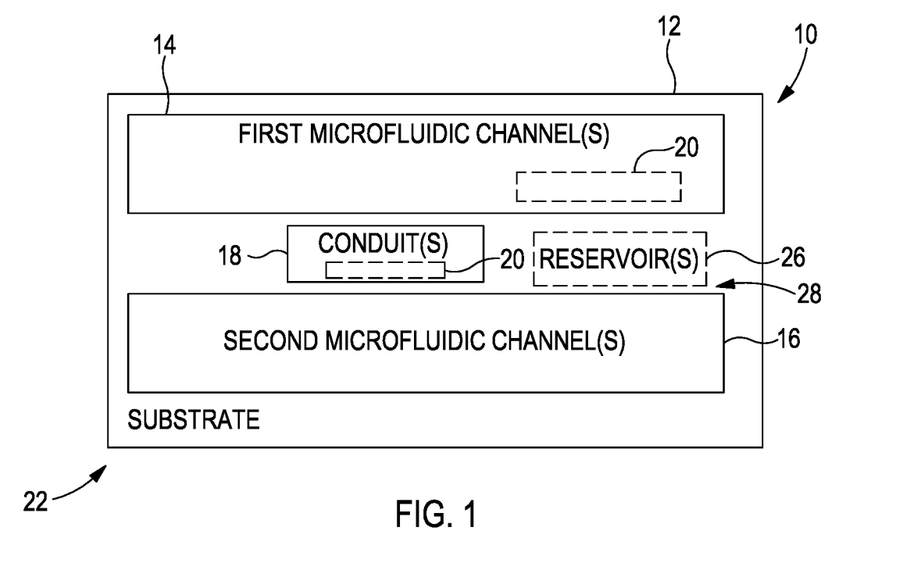
FIG. 1 shows an example of the subject-matter described herein.

FIG. 1 schematically illustrates an example of an electrode apparatus 10.

Various features referred to in relation to FIG. 1 can be found in the other figures.

In FIG. 1, the electrode apparatus 10 comprises a substrate 12, the substrate 12 comprising a first microfluidic channel 14, a second microfluidic channel 16 and at least one conduit 18 extending between the first microfluidic channel 14 and the second microfluidic channel 16.

In examples, the first microfluidic channel 14 can be considered at least one first microfluidic channel 14.

In examples, the second microfluidic channel 16 can be considered at least one second microfluidic channel 16.

The first microfluidic channel 14 and the at least one conduit 18 comprise electrically conductive material 20.

The second microfluidic channel 16 is exposed to the external environment 22 and configured to absorb liquid 24 by capillary action.

In examples, the microfluidic channels can be considered microchannels and/or microscale channels.

The electrode apparatus 10 can comprise any suitable number of first microfluidic channels 14.

The first microfluidic channel 14 comprises electrically conductive material 20 and is configured to electrically interconnect one or more of the at least one conduit 18.

The first microfluidic channel 14 is configured to allow connection of the electrode apparatus 10 to a suitable apparatus to allow, for example, one or more biopotential measurements to be made. See, for example, FIG. 9.

The first microfluidic channel 14, comprising the electrically conductive material 20, can be considered conductive microfluidic channel(s).

In examples, the first microfluidic channel 14 can have any suitable size, shape and/or form. For example, the first microfluidic channel can have any suitable size, shape and/or form to allow a large number of conduits 18 to be present in the electrode apparatus 10.

In examples the first microfluidic channel 14 can have any suitable size, shape and/or form to allow the first microfluidic channel 14 to contain electrically conductive material 20 to provide an electrical connection between the conduit(s) 18 and a measuring apparatus.

The size, shape and/or form of the first microfluidic channel 14 can be limited by the size, shape and/or form of the electrode apparatus 10.

In examples, the first microfluidic channel 14 has any suitable width.

The at least one conduit 18 extends between the first microfluidic channel 14 and the second microfluidic channel 16.

In examples, the at least one conduit 18 can be considered to link and/or connect and/or join and/or associate and/or attach and/or couple the first microfluidic channel 14 and the second microfluidic channel 16.

The at least one conduit 18 can have any suitable size, shape and/or form. In examples, the electrode apparatus 10 can comprise any suitable number of conduits 18.

In examples, one or more of the at least one conduits 18 can have different sizes, shapes and/or forms.

In examples, the one or more conduits 18 have a width in the range of 1 to 50 micrometers. However, in examples, any suitable width can be used.

In examples the one or more conduits 18 have a width to extend across multiple areas of the second microfluidic channel 16.

In some, but not necessarily all, examples, the conduit(s) 18 narrow from the first microfluidic channel 14 towards the second microfluidic channel 16.

In such examples the conduit(s) have a first width in the region of the first microfluidic channel(s) 14 and a second, smaller width in the region of the second microfluidic channel(s) 16.

The second width in the region of the second microfluidic channel(s) 16 can be in the range of 1 to 50 micrometers, with the first width in the region of the first microfluidic channel 14 being larger.

The at least one conduit 18 comprising electrically conductive material 20 is configured to function as an electrode or micro-electrode.

In examples, the conduits 18 narrow from the first microfluidic channel 14 towards the second microfluidic channel 16.

The at least one conduit 18 comprising electrically conductive material 20 can be considered to be a pin, a micro-contacting pin, a protrusion, an electrode, a micro-electrode and so on.

In examples, the at least one conduit 18 comprising electrically conductive material 20 can be considered to be exposed micro-contacting pin(s) as the end of the at least one conduit 18 is exposed to the second microfluidic channel 16.

The electrically conductive material 20 can comprise any suitable electrically conductive material or materials. For example, the electrically conductive material 20 can comprise one or more conductive materials of electrical resistivity lower than 1 Ohm·cm.

In examples, the electrically conductive material 20 comprises one or more electrically conductive fluids.

The electrically conductive material 20 can comprise one or more electrically conductive fluids. The electrically conductive fluid can be solidified once in the first microfluidic channel(s) 14 and may or may not be electrically conductive in its fluid form.

The electrically conductive fluid may be or comprise an electrically conductive ink or paste. The electrically conductive ink or paste may have a viscosity of between 1 mPa·s and 100000 mPa·s.

In examples the electrically conductive ink can comprise a nanoparticle ink, a metallo-organic decomposition ink and/or a UV-curable ink.

The electrically conductive fluid can comprise one or more of conductive silver ink(s), silver/silver chloride ink(s), silver/carbon ink(s), silver/chloride/carbon ink(s), carbon ink(s) and so on and/or any suitable combination of such ink(s) and/or any other conductive carbo-based, metal-based and/or polymer-based ink(s).

In examples, the first microfluidic channel 14 and/or the at least one conduit 18 can be considered to be filled with electrically conductive material 20.

The second microfluidic channel 16 is exposed to the external environment 22 and configured to absorb liquid 24 by capillary action.

The external environment 22 can be considered to be any environment external to the electrode apparatus 10. For example, the external environment 22 can be considered to be the environment around or adjacent to the electrode apparatus 10.

In examples the external environment 22 can be considered to be the space or volume around the electrode apparatus 10 from which the second microfluidic channel 16 can absorb liquid 24 by capillary action. For example, liquid introduced to the surface of the electrode apparatus 10 to be absorbed by the second microfluidic channel 16 can be considered to be from the external environment 22.

In examples the external environment 22 can comprise one or more surfaces, such as a subject's skin, upon which the electrode apparatus can located or placed.

The electrode apparatus 10 can comprise any suitable number of second microfluidic channels 16.

The second microfluidic channel 16 can have any suitable size, shape and/or form. For example, the second microfluidic channel can have any suitable size, shape and/or form to absorb, by capillary action, liquid from the external environment.

In examples, the second microfluidic channel 16 is located at a surface of the substrate 12 of the electrode apparatus 10 to allow the second microfluidic channel 16 to be exposed to the external environment 22.

Figure 4A:
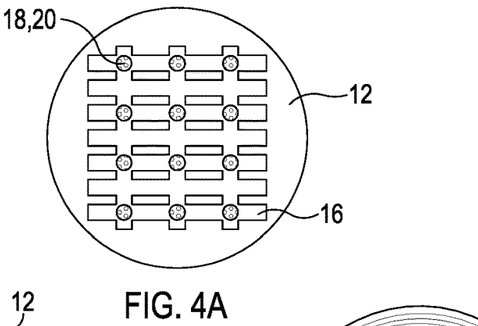
FIG. 4A to 4C shows examples of the subject-matter described herein.
Figure 4B:
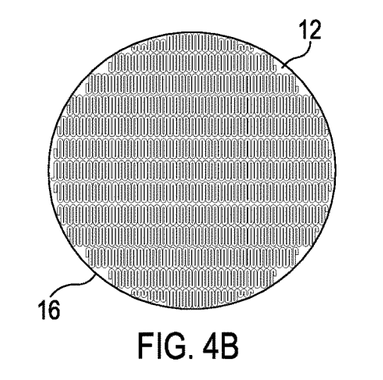
Figure 4C:
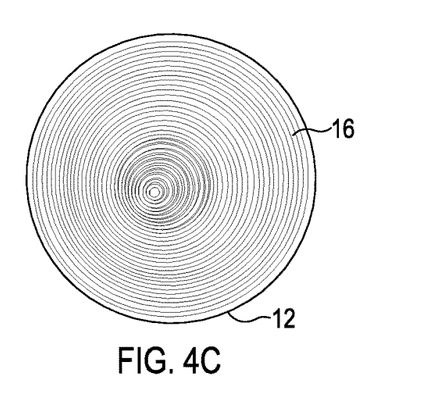

The size, shape and/or form of the second microfluidic channel can be configured to maximize the surface coverage and therefore the liquid-absorbing ability of the second microfluidic channel 16. See, for example. FIG. 4.

In examples, the second microfluidic channel 16 can be considered an open and/or empty microfluidic channel.

In examples the second microfluidic channel 16 can be considered to be an open channel as at least a portion of the second microfluidic channel 16 is at a surface of the substrate 12 and is exposed to the external environment 22 outside of the electrode apparatus 10.

In examples the second microfluidic channel 16 can be considered to be an open channel as at least a portion of the second microfluidic channel 16 is not enclosed within the electrode apparatus 10.

In examples the second microfluidic channel 16 can be configured as a trough or groove at the lower surface of the electrode apparatus 10.

In examples, the second microfluidic channel 16 can be considered to absorb liquid by capillary action and/or capillarity. Additionally or alternatively, the second microfluidic channel 16 can be considered to wick liquid that the second microfluidic channel 16 comes into contact with.

However, in examples the second microfluidic channel can be configured to absorb liquid by any suitable mechanism.

The second microfluidic channel 16 can have any suitable size to allow the second microfluidic channel(s) 16 to absorb liquid, for example, from the skin of a subject.

In examples, the second microfluidic channel 16 can be considered to be liquid absorbing microfluidic channel. The second microfluidic channel 16 can have a width in the range of 10 to 1000 micrometers. In examples the second microfluidic channel can have a width in the range of 10 to 100 micrometers.

In some examples, the second microfluidic channel 16 is configured to absorb and retain liquid which can act as an electrolyte, or electrolyte layer, for use in biopotential measurements made using the electrode apparatus 10.

In examples, the second microfluidic channel 16 can be considered to be adjacent the ends of the at least one conduit 18 to allow liquid absorbed by the second microfluidic channel 16 to be retained in position to act as an electrolyte for measurements made using the electrode apparatus 10.

In examples, an end portion of the at least one conduit/pin 18 is adjacent to/in fluidic communication with the second microfluidic channel 16.

This is advantageous as, for example, the second microfluidic channel 16 can, for example, absorb/wick sweat from a subject's body to provide a supply of liquid electrolyte for use in biopotential measurements using the electrode apparatus 10.

Accordingly, in examples, the subject can act as a source of liquid electrolyte through their sweat, which the electrode apparatus 10 can absorb/wick using the second microfluidic channel 16 for use as an electrolyte, or electrolyte layer, for biopotential measurements.

The absorption/wicking of liquid/electrolyte in this way provides for the conduit(s)/pin(s) 18 to be configured as micro-wet electrodes. In examples, the electrode apparatus 10 can comprise many conduits 18 configured to operate as micro-wet electrodes with a high density in the electrode apparatus 10. This is also advantageous.

The substrate 12 can comprise any suitable size, shape and/or form and can be comprised of any suitable material or materials.

For example, the substrate 12 can be comprised of any suitable material having natural reversible adhesion.

In examples, the substrate 12 can conform and adhere to, for example, a subject's body to allow the electrode apparatus 10 to be repeatedly used to make, for example, biopotential measurements.

In examples, the substrate 12 is formed from at least one class of conformable and/or self-adhesive polymer material.

In some examples the substrate 12 is formed from at least one of a polydimethylsiloxane classed material a polyurethane classed material, a polyfluoropolyether classed material, a polyfluoroethylene classed material, a polystyrene classed material, a polyethylene classed material, a polypropylene classed material, a polyvinyl chloride classed material, a poly(styrene-isoprene-styrene) classed material and a cellulose based material. See, for example, FIG. 8.

In examples, the electrode apparatus 10 comprises at least one reservoir 26 configured to absorb, by capillary action, liquid 24 from and/or supply, by capillary action, stored liquid 24 to of the second microfluidic channel 16.

In examples, the at least one reservoir 26 can be considered to be configured to perform at least one of absorbing, by capillary action, liquid 24 from the second microfluidic channel 16 and supplying, by capillary action, liquid stored in the at least one reservoir 26 to the second microfluidic channel 16.

This is illustrated in the example of FIG. 1 by the dashed box next to the second microfluidic channel(s) 16.

In examples, the at least one reservoir 26 comprises at least one microfluidic channel having a larger section than the second microfluidic channel 16.

In examples, having a larger section means that for a given channel length a larger volume of liquid can be stored in the reservoir 26 compared to the second microfluidic channel 16.

In examples, the at least one reservoir 26 is connected/linked to the second microfluidic channel 16 by one or more connections to allow the at least one reservoir 26 to absorb liquid 24 from and/or supply liquid 24 to the second microfluidic channel 16.

In examples, the at least one reservoir 26 comprises a plurality of connections to the second microfluidic channel 16.

In examples, the at least one reservoir 26 is enclosed within the substrate 12. This means the at least one reservoir 26 is not directly exposed to the external environment 22.

In some examples the at least one reservoir 26 can be considered to be fully enclosed within the substrate 12.

In some examples the at least one reservoir 26 can be considered to be encapsulated within the substrate 12.

The use of at least one reservoir 26 is advantageous as, for example, it allows liquid 24 absorbed via the second microfluidic channel 16 to be stored within the reservoir 26 for use when the external environment is dry. In such environments the stored liquid can then be supplied back to the second microfluidic channel 16 to ensure liquid/electrolyte is still present for use in, for example, biopotential measurements.

In some examples the at least one reservoir 26 can be preloaded with liquid 24 to allow the electrode apparatus 10 to operate in dry environments for longer.

The fluid can move automatically between the second microfluidic channel 16 and the at last one reservoir 26 by capillary action/capillarity/wicking.

The reservoir 26 can be refilled at intervals, for examples by using water, or can be refilled by absorbing excess sweat for use later, when sweat is not present. This can, for example, improve skin contact for biopotential measurements.

Accordingly, in examples, the electrode apparatus 10 can be considered to be a dry electrode that acts or operates as a wet electrode.

In examples, the electrode apparatus can be considered to be activated when liquid 24 is present in the second microfluidic 16 channel. In examples the electrode apparatus can be activated prior to use by applying liquid 24 to the second microfluidic channel 16.

In some examples, an apparatus comprising one or more microfluidic channels and one or more reservoirs can be used to maintain low contact resistance, for example, in scenarios where electrical connection is not easily accessed for maintenance.

Additionally or alternatively, such a system can be used with deoxidizing additive in the liquid which could help to maintain an electrical connection for contacts which are subject to corrosion.

Figure 2A:
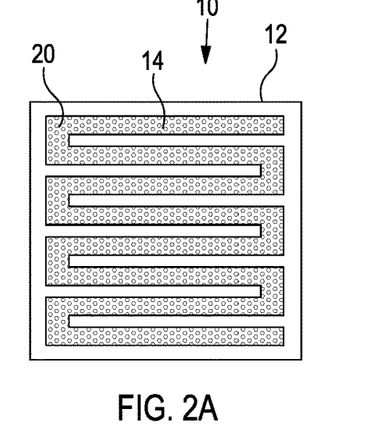
FIG. 2A to 2C shows examples of the subject-matter described herein.
Figure 2B:
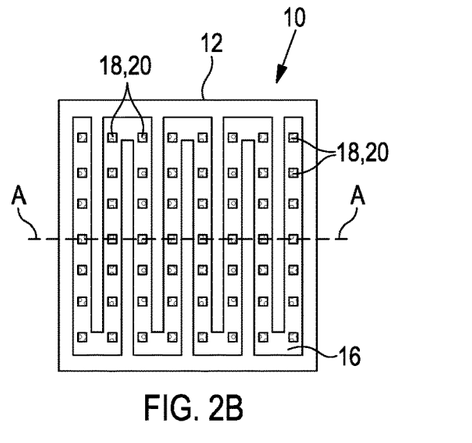
Figure 2C:
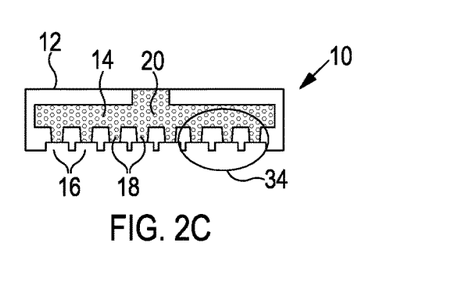

FIG. 2 illustrates an example of an electrode apparatus 10. One or more elements of the electrode apparatus 10 can be as described in relation to FIG. 1.

FIG. 2, part A, illustrates a top view of the electrode apparatus 10.

In the illustrated view the upper surface of the substrate 12 is not shown and the first microfluidic channel 14 comprising electrically conductive material 20 can be seen.

However, in examples, the substrate 12 of the electrode apparatus 10 does not comprise material covering the upper surface of the electrode apparatus 10.

In the illustrated example, the electrode apparatus 10 comprises a single, continuous first microfluidic channel 14 comprising electrically conductive material 20.

However, in examples, the electrode apparatus 10 can comprise any suitable number of separate first microfluidic channels 14.

The first microfluidic channel 14 is shaped in a form that repeatedly turns back on itself.

Part B of FIG. 2 illustrates a bottom view of the electrode apparatus 10.

In part B of FIG. 2 the second microfluidic channel 16 can be seen. In the example of FIG. 2 the second microfluidic channel 16 comprises a single continuous microfluidic channel 16 having a similar shape as the first microfluidic channel 14, but rotated by 90°.

However, in examples, the electrode apparatus 10 can comprise any suitable number of separate second microfluidic channels 16.

In the example of part B of FIG. 2 the ends of the conduits 18, comprising electrically conductive material 20, can also be seen.

In the example of FIG. 2 the conduits 18 are substantially regularly spaced. However, in examples, any suitable number and/or layout/configuration of conduits 18 can be used.

In the example of FIG. 2 the conduits/pins 18 are spaced substantially evenly or regularly along the length of the first and second microfluidic channels 14, 16.

The second microfluidic channel 16 is exposed to the external environment 22. In the example of FIG. 2, the second microfluidic channel 16 is located at the lower surface of the substrate 12 of the electrode apparatus 10 allowing the second microfluidic channel 16 to be exposed to the external environment 22.

Part C of the example of FIG. 2 illustrate a cross-section through the electrode apparatus 10 taken at the dashed line indicated A-A in part B of FIG. 2.

In part C of FIG. 2 a plurality of conduits 18 comprising conductive material 20 can be seen extending between the first microfluidic channel 14 and the second microfluidic channel 16.

The ends of the conduits 18 are adjacent/proximate to the open, second microfluidic channel 16.

Accordingly, the ends/end portions of the conduits 18 are in fluidic communication with the second microfluidic channel 16 which is exposed to the external environment 22.

If the electrode apparatus 10 exposed to liquid 24 at the lower surface, the second microfluidic channel 16 will absorb the liquid 24 which can then act as an electrolyte layer in, for example, the use of the electrode apparatus 10, providing a sustained low-impedance interface to make low-noise biopotential measurements.

For example, if the electrode apparatus 10 is placed on the skin of a subject the second microfluidic channel 16 can absorb/wick sweat from the subject, the sweat acting as an electrolyte layer in between the electrically conductive conduits 18 of the electrode apparatus 10 and the skin.

Figure 3A:
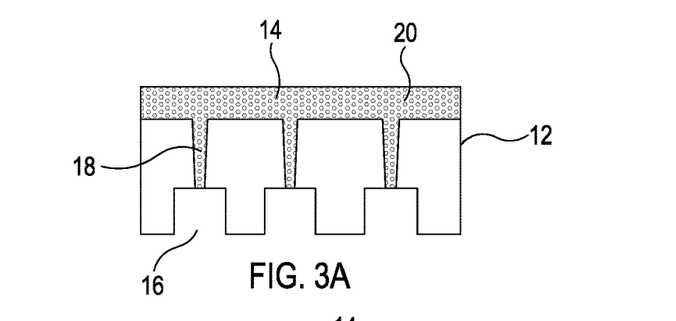
FIGS. 3A & 3B shows examples of the subject-matter described herein.
Figure 3B:
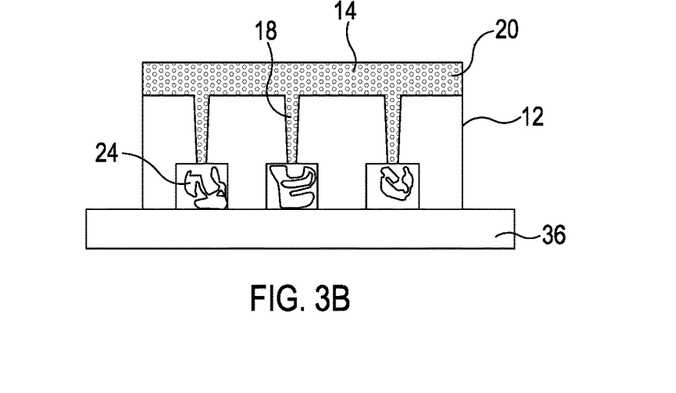

An area 34 of the electrode apparatus 10 in part C of FIG. 2 is circled. The highlighted area 34 is enlarged in the example of FIG. 3.

FIG. 3 illustrates an enlarged section of the electrode apparatus 10 illustrated in the example of FIG. 2.

In part A of FIG. 3 the lower portion of the electrode apparatus 10 is shown.

In the illustrated example, three conduits/pins 18 can be seen adjacent to portions of the second microfluidic channel 16.

In part A of FIG. 3 the second microfluidic channel 16 is empty.

In part B of FIG. 3, the electrode apparatus 10 has been placed on the skin 36 of a subject.

In part B of FIG. 3 liquid 24 has been absorbed by the second microfluidic channel 16 from the skin 36 of the subject.

The absorbed liquid 24 acts as an electrolyte layer, between the electrically conductive conduits 18 of the electrode apparatus 10 and the skin, in biopotential measurement using the electrode apparatus 10.

That is, in examples, the dry electrode apparatus 10 can be placed on the skin and the activation of the electrode apparatus 10 happens over a period of time in which sweat is absorbed into the second microfluidic channel(s) 16.

In examples, the electrode apparatus 10 can be activated prior to placing it on the skin of a subject. For example, this can be done by introducing liquid 24 to the lower surface of the electrode apparatus 10 in any suitable way. In examples, a moist towel can be wiped on the lower surface and/or liquid sprayed on the bottom face of the electrode apparatus 10. Then, the second microfluidic channel(s) 16 can absorb the liquid 24 by capillary action.

In examples, the electrode apparatus 10 illustrated in FIGS. 2 and 3 can comprise one or more reservoirs 26 (not illustrated).

FIG. 4 illustrates examples of an electrode apparatus 10. One or more elements of the electrode apparatus 10 illustrated in FIG. 4 can be as described in relation to FIG. 1.

The examples of FIG. 4 show bottom views of the electrode apparatus 10.

In part A of FIG. 4, the second microfluidic channel 16 and the ends of the at least one conduit 18 comprising electrically conductive material 20 can be seen.

Part A of FIG. 4 is similar to part B of FIG. 2, however in part A of FIG. 4 the second microfluidic channel 16 comprises a crosshatch pattern with fewer conduits 18 regularly spaced around the second microfluidic channel 16.

Parts B and C of FIG. 4 illustrate two further examples of the second microfluidic channel 16.

In the examples of parts B and C of FIG. 4 the second microfluidic channels 16 are designed to maximise surface coverage to enhance the liquid absorbing ability of the microfluidic channel network, which in turn can, for example, reduce noise during biopotential measurements.

In part B of FIG. 4 the second microfluidic channel 16 has a repeating meandering/serpentine pattern of an extended S.

In part C of FIG. 4 the second microfluidic channel 16 comprises a series of circles.

In parts B and C of FIG. 4 the conduits/pins 18 are not shown for the sake of clarity.

Figure 5A:
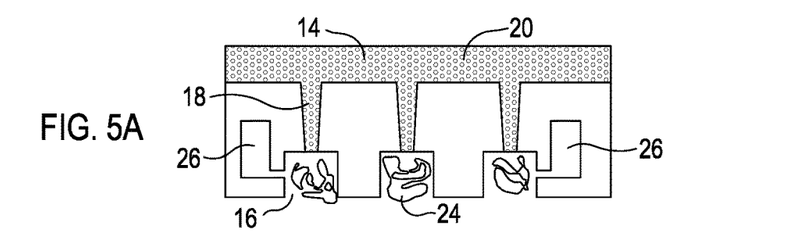
FIG. 5A to 5C shows examples of the subject-matter described herein.
Figure 5B:
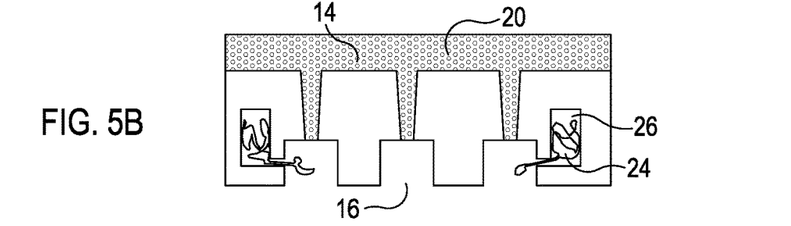
Figure 5C:
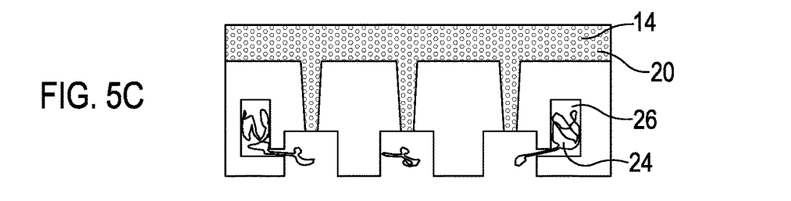

FIG. 5 illustrates an example of part of an electrode apparatus 10. One or more elements of the electrode apparatus 10 can be as described in relation to FIG. 1.

The examples illustrated in FIG. 5 show an enlarged section of an electrode apparatus 10. The examples illustrated in FIG. 5 are similar to those illustrated in FIG. 3.

However, in the examples of FIG. 5 the electrode apparatus 10 comprises two reservoirs 26. In examples, any suitable number of reservoirs 26 can be used.

In the examples illustrated in FIG. 5 the reservoirs 26 are large-section microfluidic channels enclosed within the substrate 12. Therefore, the reservoirs 26 are not directly exposed to the external environment 22, but are in fluidic communication with the external environment 22 via the microfluidic channel 16.

In part A of FIG. 5 liquid 24 is present in the second microfluidic channel 16. The liquid 24 can be present as a result of application of liquid onto the electrode 10 and/or absorption/wicking of liquid/sweat from a subject's skin.

In part A of FIG. 5 the reservoirs 26 are empty.

In part B of FIG. 5 the liquid 24 flows into the reservoirs 26 by capillary action.

In part C of FIG. 5 the liquid 24 stored within the reservoirs 26 is supplied back to the second microfluidic channel 16 when the second microfluidic channel 16, exposed to a dry environment for a time, is about to become depleted of liquid 24. This ensures continuous presence of liquid 24 within the second microfluidic channel 16, liquid 24 which acts as an electrolyte layer in between the electrically conductive conduits 18 and the external environment 22, for example the skin 36 of the subject when the electrode apparatus 10 is placed on the subject 10.

In examples, the reservoirs 26 have a plurality of connections to the second microfluidic channel 16 allowing liquid 24 to move freely throughout the network of reservoirs and second microfluidic channel(s) 16 without clogging and/or becoming airlocked.

Figure 6:
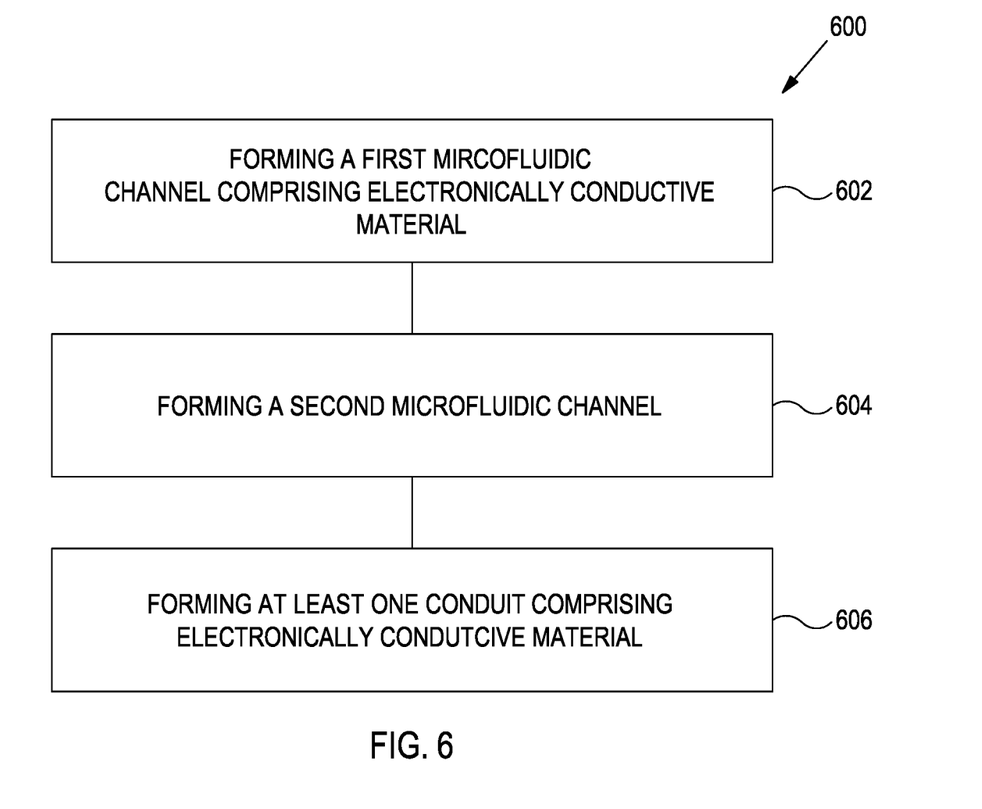
FIG. 6 shows an example of the subject-matter described herein.

FIG. 6 illustrates an example of a method 600. In the example of FIG. 6, the method 600 is a method of forming an electrode apparatus 10.

In examples, the method 600 can be considered a method of fabricating and/or providing and/or manufacturing an electrode apparatus 10.

Accordingly, where the term form, forming and so on is used it should be understood that this is intended to also include provide/providing, manufacture/manufacturing, fabricate/fabricating and so on.

In examples, the electrode apparatus 10 can be as described herein. For example, the electrode apparatus 10 can be as described in relation to at least one of FIGS. 1, 2, 3, 4 and/or 5.

At block 602 a first microfluidic channel 14 comprising electrically conductive material 20 is formed.

In examples at least one first microfluidic channel 14 comprising electrically conductive material 20 is formed.

Any suitable method for forming a first microfluidic channel 14 comprising electrically conductive material 20 can be used. For example, a substrate 12 can be formed comprising a microfluidic channel 14 and electrically conductive material 20 introduced/provided to the first microfluidic channel 14.

In examples any suitable method to form a first microfluidic channel 14 within the substrate 12 can be used. For example, any suitable layer-by-layer assembly approach can be used to form the substrate 12. In examples, soft lithography fabrication techniques can be used to form the first microfluidic channel 14 in the corresponding layers of the substrate 12.

In some examples, electrically conductive material 20 can be provided in the shape of the first microfluidic channel 14 and a substrate 12 provided around the electrically conductive material 20.

Any suitable method for providing electrically conductive material 20 in the shape of the first microfluidic channel 14 can be used. In examples, the electrically conductive material 20 can be printed in the shape of the first microfluidic channel 14, for example using any suitable three-dimensional printing technique.

In examples, any suitable method of forming the substrate 12 around the first microfluidic channel(s) 14 can be used. For example, the substrate can be cast around the existing channel(s) 14.

At block 604 a second microfluidic channel 16 is formed, the second microfluidic channel exposed to the external environment and configured to absorb liquid 24 by capillary action.

In examples at least one second microfluidic channel 16 is formed, the at least one second microfluidic channel exposed to the external environment and configured to absorb liquid 24 by capillary action.

Any suitable method for forming a second microfluidic channel 16 can be used.

For example, a substrate 12 can be formed comprising the second microfluidic channel 16.

In examples any suitable method to form the second microfluidic channel 16 within the substrate 12 can be used. For example, any suitable layer-by-layer assembly approach can be used to form the substrate 12. In examples, soft lithography fabrication techniques can be used to form the second microfluidic channel 16 in the corresponding layers of the substrate 12.

In some examples, removable mould material can be provided in the shape of the second microfluidic channel 16, a substrate 12 provided around the material and then the material removed to leave empty the second microfluidic channel 16 in the substrate 12.

Any suitable method for providing material in the shape of the second microfluidic channel 16 can be used. In examples, the removable mould material can be printed in the shape of the second microfluidic channel 16, for example using any suitable three-dimensional printing technique.

In examples, any suitable method of forming the substrate 12 around the second microfluidic channel(s) 16 can be used. For example, the substrate can be cast around the existing channel(s) 16.

In examples, any suitable method for removing removable mould material in the shape of the second microfluidic channel can be used. In examples, the removable mould material can be removed by dissolving the material using any suitable solvent.

At block 606 the at least one conduit 18 extending between the first microfluidic channel 14 and the second microfluidic channel 16 is formed, the at least one conduit comprising electrically conductive material 20.

Any suitable method for forming the at least one conduit 18 extending between the first microfluidic channel 14 and the second microfluidic channel 16 and comprising electrically conductive material 20 can be used.

For example, any suitable method can be used to form the at least one conduit 18 in the corresponding layers of the substrate 12.

For example, a substrate 12 can be formed comprising at least one conduit 18 and electrically conductive material 20 introduced/provided to the at least one conduit 18.

In examples any suitable method to form the substrate 12 can be used. For example, any suitable layer-by-layer assembly approach can be used to form the substrate 12. In examples, soft lithography fabrication techniques can be used.

Any suitable method for introducing the electrically conductive material 20 into the first microfluidic channel 14 and conduits 18 can be used.

For example, the electrically conductive material 20 can be squeegeed into the first microfluidic channel 14 and/or conduits 18. Additionally or alternative, a vacuum pump or a pressure press can be used to push the electrically conductive material 20 into the apparatus.

In examples, electrically conductive material 20 can be provided in the shape of the at least one conduit 18 and a substrate 12 formed around the at least one conduit 18.

Any suitable method for providing electrically conductive material 20 in the shape of the at least conduit 18 can be used. In examples, the electrically conductive material 20 can be printed in the shape of the at least one conduit 18, for example using any suitable three-dimensional printing technique.

Accordingly, in examples, forming the first microfluidic channel 14 and forming the at least one conduit 18 comprise fabricating electrically conductive material 20 in the form of the first microfluidic channel 14 and at least one conduit 18.

In examples, forming a second microfluidic channel 16 comprises fabricating removable mould material in the form of the second microfluidic channel 16. In some examples the removable mould material comprises soluble mould material 30.

In examples, the method 600 comprises forming a substrate around the formed first microfluidic channel 14, second microfluidic channel 16 and at least one conduit 18.

In examples, the method 600 comprises removing the removable mould material. In some examples the method 600 comprises dissolving soluble mould material by using any suitable solvent.

Accordingly, there is provided a method 600 comprising:
forming a first microfluidic channel 14 comprising electrically conductive material 20;
forming a second microfluidic channel 16; and
forming at least one conduit 18 extending between the first microfluidic channel 14 and second microfluidic channel 16, the at least one conduit 18 comprising electrically conductive material 20;
wherein the second microfluidic channel 16 is exposed to the external environment 22 and configured to absorb liquid 24 by capillary action.

In examples, there is provided a method 600 comprising fabricating electrically conductive material in the form of a first microfluidic channel 14 and at least one conduit 18, fabricating removable mould material in the form of a second microfluidic channel 16, forming a substrate 12 around the formed first microfluidic channel 14, second microfluidic channel 16 and at least one conduit 18 and removing the removable mould material.

In some examples, forming the first microfluidic channel 14, the second microfluidic channel 16 and the at least one conduit 18 comprises forming a substrate 12 layer by layer to form the first microfluidic channel 14, the second microfluidic channel 16 and at least one conduit 18; and providing electrically conductive material 20 in the first microfluidic channel 14 and the at least one conduit 18.

Accordingly, examples provide for a method that comprises forming a substrate 12 layer by layer to form a first microfluidic channel 14 and at least one conduit 18, the at least one conduit 18 extending between the first microfluidic channel 14 and second microfluidic channel 16, and introducing/providing electrically conductive material in the first microfluidic channel 14 and the at least one conduit 18.

In examples, the method comprises forming at least one reservoir 26 configured to perform at least one of absorbing, by capillary action, liquid 24 from the second microfluidic channel 16 and supplying, by capillary action, liquid stored in the at least one reservoir 26 to the second microfluidic channel 16.

In examples the method can be considered to comprise forming at least one reservoir 26 configured to absorb, by capillary action, liquid 24 from and/or supply liquid stored in the at least one reservoir 26 to the second microfluidic channel 16.

Any suitable method for forming at least one reservoir 26 configured to perform at least one of absorbing, by capillary action, liquid 24 from the second microfluidic channel 16 and supplying, by capillary action, liquid stored in the reservoir 26 to the second microfluidic channel 16 can be used.

For example, a substrate 12 can be formed comprising the at least one reservoir 26.

In examples, removable mould material can be provided in the form of the at least one reservoir 26 and a substrate 12 formed around the material with the material subsequently being removed.

In examples, one or more blocks of the method 600 can be altered or omitted. For example, the order of one or more actions can be altered and/or one or more actions omitted.

Additionally or alternatively one or more actions of method 600 can be combined. For example, blocks 602 and 606 can be combined.

FIG. 7 schematically illustrates an example of a method 700. In the illustrated example, the method 700 is a method of forming an electrode apparatus 10.

In the example, the electrode apparatus 10 can be as described herein.

The left side of FIG. 7 illustrates a cross-sectional view of the electrode apparatus 10 and the right side shows a perspective view.

Part A of FIG. 7 illustrates a layer-by-layer assembly of a first microfluidic channel 14, a plurality of conduits 18 and an upper surface of the substrate 12.

In the perspective view of part A of FIG. 7 the plane 42 is shown from which the cross-sectional view is taken.

Figure 7A:
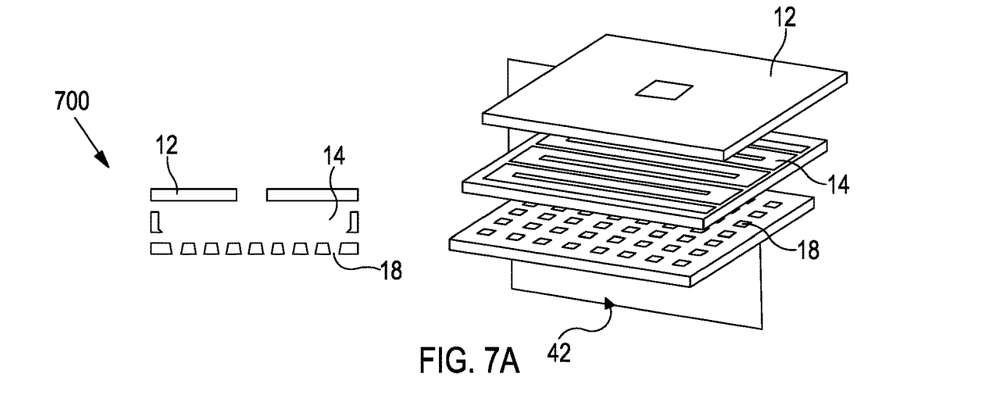
FIG. 7A-7E shows an example of the subject-matter described herein.

Any suitable layer by layer assembly approach can be used to form the substrate 12. For example, each layer can be fabricated using standard soft lithography fabric techniques.

In part B of FIG. 7 a support 38 is introduced at the bottom of the electrode apparatus 10 and electrically conductive material 20 provided in the first microfluidic channel 14 and conduits 18.

Figure 7B:
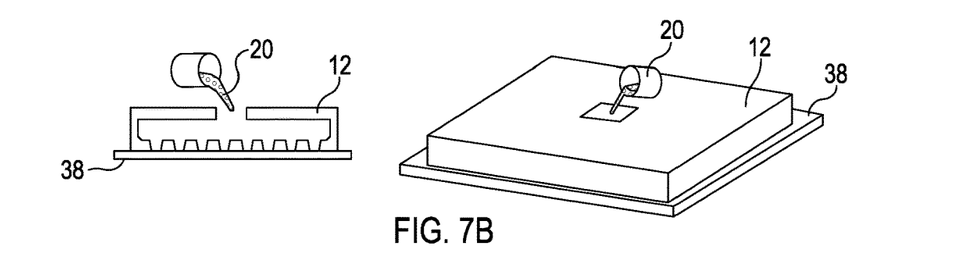
Figure 7C:
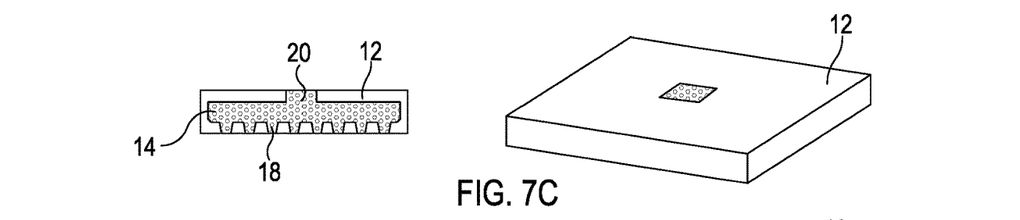
Figure 7D:
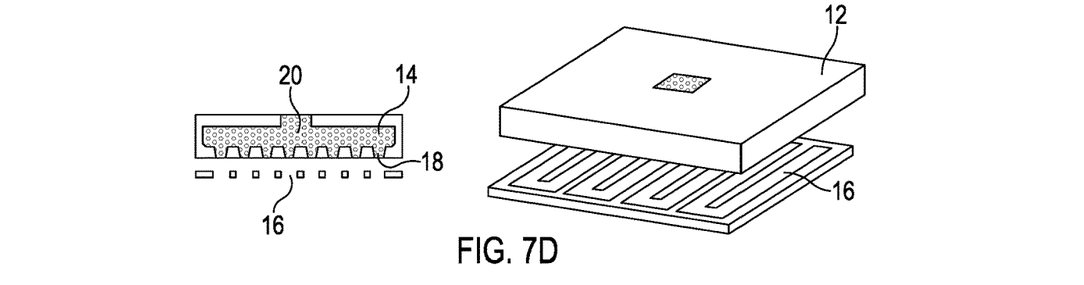
Figure 7E:
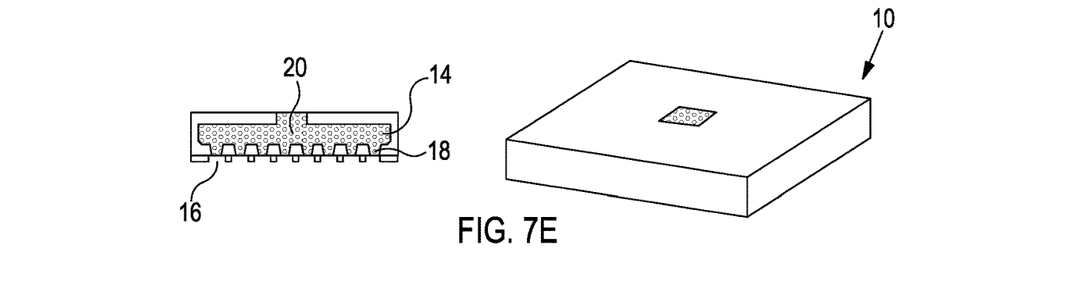

In the illustrated example, the electrically conductive material 20 is introduced via an aperture in the upper surface of the substrate 12.

Any suitable method for introducing the electrically conductive material 20 into the first microfluidic channel 14 and conduits 18 can be used.

For example, the electrically conductive material 20 can be squeegeed into the first microfluidic channel 14 and/or conduits 18. Additionally or alternatively, a vacuum pump or a pressure press can be used to push the electrically conductive material 20 into the apparatus.

When the electrically conductive material 20 has been introduced into the first microfluidic channel 14 and conduits 18 the electrically conductive material 20 can, in examples, be solidified and/or cured and the support 38 at the bottom removed.

The result of this can be seen in part C of FIG. 7 in which the substrate 12 comprises a first microfluidic channel 14 and a plurality of conduits 18 comprising electrically conductive material 20.

At part D of FIG. 7 a second microfluidic channel 16 is formed in a further layer and added to the formed apparatus to provide the electrode apparatus 10 comprising a first microfluidic channel 14, second microfluidic channel 16 and a plurality of conduits 18, the first microfluidic channel 14 and conduits 18 comprising electrically conductive material 20 as illustrated in part E of FIG. 7.

As can be seen in FIG. 7 the second microfluidic channel 16 is adjacent to the ends of the conduits 18 and located at the bottom surface of the substrate 12 to allow the second microfluidic channel 16 to be exposed to the external environment 22.

In examples, one or more blocks of the method 700 can be altered or omitted.

Figure 8:
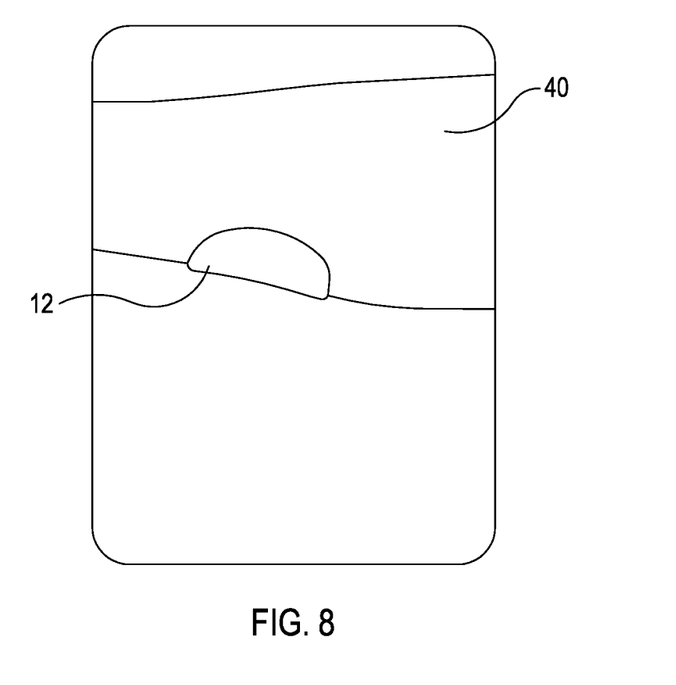
FIG. 8 shows an example of the subject-matter described herein.

FIG. 8 illustrates an example of a substrate material 12.

In the example of FIG. 8, a substrate material 12 is located on the arm 40 of a subject.

In the illustrated example, the substrate 12 is a PDMS-substrate material which has natural reversible adhesion and can therefore be removed and placed on a subject's arm 40 repeatedly.

The substrate material 12 can be placed onto the skin without any additives or adhesives.

Accordingly, an electrode apparatus 10 formed in a substrate 12 illustrated in the example of FIG. 8 can be applied to the skin of a subject multiple times without any additives or adhesives while providing a high number of electrodes in the substrate material 12.

The natural tendency of the material to adhere to the skin provides the benefit of better skin contact in contact-based biopotential measurements such as EMG, ECG, EEG and so on without, for example, the need for tightening straps.

In addition, PDMS, for example, is safe to use on the skin, can be sterilized and is resistant to bacterial growth.

Figure 9:
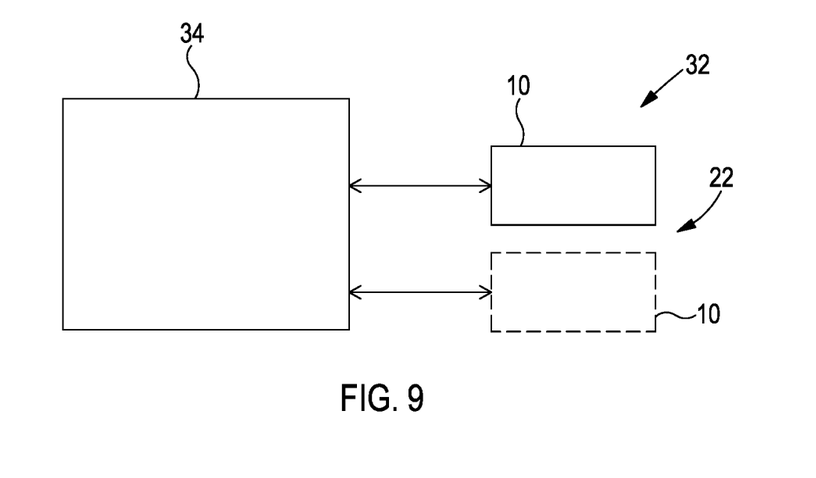
FIG. 9 shows an example of the subject-matter described herein.

FIG. 9 illustrates an example of a system 32.

In the example of FIG. 9 the system 32 comprises an apparatus for making one or more biopotential measurements 34 and; at least one electrode apparatus 10 as described herein.

For example, the at least one electrode apparatus 10 can be as described in relation to one or more of FIGS. 1 to 7.

In examples, the at least one electrode apparatus 10 is placed on a subject's body to enable one or more biopotential measurements to be made.

Any suitable apparatus for making one or more biopotential measurements 34 can be used. For example, biopotential amplifier implementation and/or amplifier microchip system can be used.

In the example of FIG. 9, information can be passed between the electrode apparatus 10 and the at least one apparatus for making one or more biopotential measurements 34 to allow one or more measurement to be made. This is illustrated by the double-ended arrow between the apparatus 34 and the electrode apparatus 10.

The electrode apparatus 10 is operationally coupled to the apparatus 34 and any number of intervening elements can be present, including no intervening elements.

In examples, any suitable connection for transferring information between the apparatus 34 and the electrode apparatus 10 can be used.

In examples, the electrode apparatus 10 is connected to the apparatus 34 via one or more wires and/or wireless connections.

In examples, the system 32 can comprise any suitable number of electrode apparatus 10. For example, the system 32 can comprise arrays of electrode apparatus 10 connected to the apparatus 34.

This is illustrated in the example of FIG. 9 by the dashed box indicating one or more electrode apparatus 10.

In examples, there is provided a wearable electronic device comprising one or more electrode apparatus as described herein and/or one or more systems 32 as described herein.

In examples, the wearable electronic device comprises a device for fitness tracking and/or smart clothing.

Examples of the disclosure are advantageous. Examples provide for an electrode apparatus 10 that can self-adhere to skin, is not size limited and is comfortable to wear and is functionally sustainable to provide long-term continuous tracking of, for example, biopotential information.

Examples provide for an electrode apparatus 10 that does not require gel and adhesive layers but can perform as a sticky wet gel electrode.

Additionally or alternatively, examples provide for an electrode apparatus 10 that can be used in applications where the electrode needs to go on and come off the skin many times without leaving a residue.

Examples provide for an electrode apparatus 10 that can be integrated into smart garments to measure biopotential measurements.

In examples the electrode apparatus 10 can be washed and dried as is done for other garments.

In examples the electrode apparatus 10 can be used in electromyograms (EMG) and can be used for gesture recognition for controlling devices or for controlling things in virtual reality among other things.

The blocks illustrated in the FIGS. 6 and 7 may represent steps in a method. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer and exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An electrode apparatus comprising:
    a substrate, the substrate being formed from an adhesive material and comprising:
        a first microfluidic channel at a first surface of the substrate;
        a second microfluidic channel at an opposing second surface of the substrate; and
        at least one conduit extending internal to the substrate between the first microfluidic channel and the second microfluidic channel;
        an electrically conductive material filling the first microfluidic channel and the at least one conduit; and
        wherein the second microfluidic channel is exposed to the external environment at a skin-facing surface at the opposing second surface of the substrate, the skin-facing surface comprising a plurality of at least one of troughs or grooves, the skin-facing surface being configured to be placed onto the skin of a body of a subject, the second microfluidic channel being configured to absorb liquid by capillary action by non-invasive placement of the substrate directly onto the body of the subject.

2. The electrode apparatus as claimed in claim 1, comprising at least one reservoir configured to perform at least one of absorbing, by capillary action, liquid from the second microfluidic channel and supplying, by capillary action, liquid stored in the at least one reservoir to the second microfluidic channel.

3. The electrode apparatus as claimed in claim 2, wherein the at least one reservoir comprises at least one microfluidic channel having a larger section than the second microfluidic channel.

4. The electrode apparatus as claimed in claim 2, wherein the at least one reservoir comprises a plurality of connections to the second microfluidic channel.

5. The electrode apparatus as claimed in claim 2, wherein the at least one reservoir is enclosed within the substrate.

6. The electrode apparatus as claimed in claim 1, wherein the conduits narrow from the first microfluidic channel towards the second microfluidic channel.

7. The electrode apparatus as claimed in claim 1, wherein the substrate is formed from at least one class of conformable and/or self-adhesive polymer material.

8. A method comprising:
    forming a first microfluidic channel comprising electrically conductive material at a first surface in a substrate formed from an adhesive material;
    forming a second microfluidic channel at a second surface in the substrate formed from the adhesive material, the second surface opposing the first surface; and
    forming at least one conduit internal to the substrate and extending between the first microfluidic channel and the second microfluidic channel, the at least one conduit comprising an electrically conductive material filling the first microfluidic channel and the at least one conduit;

wherein the second microfluidic channel is exposed to the external environment at a skin-facing surface at the second surface of the substrate opposing the first surface, the skin-facing surface of the second microfluidic channel comprising a plurality of at least one of troughs or grooves, the skin-facing surface being configured to be placed onto the skin of a body of a subject, the second microfluidic channel being configured to absorb liquid by capillary action by non-invasive placement directly onto the body of the subject.

9. A method as claimed in claim 8, wherein forming the first microfluidic channel and forming the at least one conduit comprises fabricating electrically conductive material in the form of the first microfluidic channel and at least one conduit.

10. A method as claimed in claim 8, wherein forming the second microfluidic channel comprises fabricating removable mould material in the form of the second microfluidic channel.

11. A method as claimed in claim 9, comprising forming the substrate around the formed first microfluidic channel, second microfluidic channel and at least one conduit.

12. A method as claimed in claim 10, comprising removing the removable mould material.

13. A method as claimed in claim 8, wherein forming the first microfluidic channel, the second microfluidic channel and the at least one conduit comprises:

forming the substrate layer by layer to form the first microfluidic channel, the second microfluidic channel and at least one conduit; and providing electrically conductive material in the first microfluidic channel and the at least one conduit.

14. A method as claimed in claim 8, comprising forming at least one reservoir configured to perform at least one of absorbing, by capillary action, liquid from the second microfluidic channel and supplying, by capillary action, the second microfluidic channel.

15. A system comprising:

an apparatus for making one more biopotential measurements; and an electrode apparatus comprising a substrate, the substrate comprising a first microfluidic channel formed in an adhesive material at a first surface of the substrate; a second microfluidic channel formed in the adhesive material at a second surface opposing the first surface; at least one conduit extending internal to the substrate between the first microfluidic channel and the second microfluidic channel; and an electrically conductive material filling the first microfluidic channel and the at least one conduit; and wherein the second microfluidic channel is exposed to the external environment at a skin-facing surface at the opposing second surface of the substrate, the skin-facing surface of the substrate comprising a plurality of at least one of troughs or grooves, the skin-facing surface being configured to be placed onto the skin of a body of a subject, the second microfluidic channel being configured to absorb liquid by capillary action by non-invasive placement of the substrate directly onto the body of the subject.

16. The system as claimed in claim 15, comprising at least one reservoir configured to perform at least one of absorbing, by capillary action, liquid from the second microfluidic channel and supplying, by capillary action, liquid stored in the at least one reservoir to the second microfluidic channel.

17. The system as claimed in claim 16, wherein the at least one reservoir comprises at least one microfluidic channel having a larger section than the second microfluidic channel.

18. The system as claimed in claim 16, wherein the at least one reservoir comprises a plurality of connections to the second microfluidic channel.

19. The system as claimed in claim 16, wherein the at least one reservoir is enclosed within the substrate.

20. The system as claimed in claim 15, wherein the conduits narrow from the first microfluidic channel towards the second microfluidic channel.

\* \* \* \* \*